US012674775B2

(12) United States Patent
Wang et al.

(10) Patent No.: US 12,674,775 B2
(45) Date of Patent: Jul. 7, 2026

(54) NON-REAGENT CHLORIDE ANALYSIS IN ACID COPPER PLATING BATHS

(71) Applicant: KLA Corporation, Milpitas, CA (US)

(72) Inventors: Jingjing Wang, Livingston, NJ (US); Patrick Saitta, Brooklyn, NY (US); Eugene Shalyt, Washington Township, NJ (US)

(73) Assignee: KLA Corporation, Milpitas, CA (US)

( * ) Notice: Subject to any disclaimer, the term of this patent is extended or adjusted under 35 U.S.C. 154(b) by 166 days.

(21) Appl. No.: 18/482,443

(22) Filed: Oct. 6, 2023

(65) Prior Publication Data

US 2024/0125730 A1    Apr. 18, 2024

Related U.S. Application Data

(60) Provisional application No. 63/417,318, filed on Oct. 18, 2022.

(51) Int. Cl.
| | |
|---|---|
| *G01N 27/333* | (2006.01) |
| *G01N 1/38* | (2006.01) |
| *G01N 27/44* | (2006.01) |
| *G01N 33/18* | (2006.01) |

(52) U.S. Cl.
CPC ............. *G01N 27/333* (2013.01); *G01N 1/38* (2013.01); *G01N 27/44* (2013.01); *G01N 33/1813* (2013.01)

(58) Field of Classification Search
CPC .... G01N 27/333; G01N 27/42; G01N 27/423; G01N 27/44; G01N 1/38; G01N 33/1813
See application file for complete search history.

(56) References Cited

U.S. PATENT DOCUMENTS

| | | | |
|---|---|---|---|
| 6,709,561 | B1 | 3/2004 | Pavlov et al. |
| 7,205,153 | B2 | 4/2007 | Balisky |
| 7,229,543 | B2 | 6/2007 | Graham et al. |
| 7,291,253 | B2 | 11/2007 | Pavlov et al. |
| 8,118,988 | B2 | 2/2012 | Shalyt et al. |
| 8,142,640 | B2 | 3/2012 | Pavlov et al. |
| 8,535,504 | B2 | 9/2013 | Pavlov et al. |
| 10,407,795 | B2 | 9/2019 | Parekh et al. |
| 2004/0203165 | A1 | 10/2004 | Balisky |
| 2007/0224086 | A1 | 9/2007 | Hayashi et al. |

(Continued)

FOREIGN PATENT DOCUMENTS

| | | | |
|---|---|---|---|
| CN | 105136894 | B | 10/2017 |
| CN | 112985946 | B | 3/2022 |

(Continued)

OTHER PUBLICATIONS

Definition of "titrant" posted by inorganic ventures, downloaded Aug. 20, 2025, from https://www.inorganicventures.com/technical-glossary/titrant (Year: 2025).*

(Continued)

*Primary Examiner* — Alexander S Noguerola
(74) *Attorney, Agent, or Firm* — Baker Botts L.L.P.

(57) ABSTRACT

The disclosed subject matter relates to techniques for methods and systems for non-reagent chloride analysis in an acid copper plating bath, using a blend of VMS (Virgin Makeup Solution) to generate $Ag^+$-containing solution as a titration into a sample.

10 Claims, 3 Drawing Sheets

(56) References Cited

U.S. PATENT DOCUMENTS

| | | |
|---|---|---|
| 2009/0065362 A1 | 3/2009 | Pavlov et al. |
| 2019/0094198 A1 | 3/2019 | Kidd, IV |
| 2021/0025842 A1 | 1/2021 | Hawsah |

FOREIGN PATENT DOCUMENTS

| | | | | |
|---|---|---|---|---|
| EP | 1431424 A2 * | 8/2004 | .............. | C25D 7/12 |
| JP | 4335723 B2 | 9/2009 | | |
| KR | 20120064907 A | 6/2012 | | |
| WO | WO 2017/175953 A1 | 10/2017 | | |

OTHER PUBLICATIONS

Ramsay et al., "Electrometric Titration of Chloride in Small Volumes," J. Exp. Biol., 32(4), pp. 822-829, 1955 (Year: 1955).*
Thermoscientific, Smart Tips Log #148, "Choosing the Best Method for ISE Measurement of Your Sample: A simple guide for testing ions in various sample types," 2016 (Year: 2016).*
Omega Technologies, ISE-8760 & ISE-8770 Chloride Ion Selective Electrodes—Operator's Manual M791/0892, 1993 (Year: 1993).*
Application Bulletin 130/4 e, Chloride titrations with potentiometric indication, Competence Center Titration, Metrohm International Headquarters, 6 pages (May 23, 2013).
Cedergren et al., "Trace Analysis for Chlorinated Hydrocarbons in Air by Quantitative Combustion and Coulometric Chloride Determination: Application to Standardization of Vinyl Chloride Permeation Tubes," Talanta. 23(3):217-223 (1976).
Cedergren et al., "Coulometric Trace Determination of Chloride," Talanta 18(9):917-925 (1971).
Jacobsen et al., "A Simple Coulometric Method for the Determination of Chloride in Natural Water," Analytica Chimica Acta. 64(2):280-283 (1973).
Kaiser et al., "Determination of chloride in acid copper plating bath," ThermoFisher Scientific, 2017, 3 pgs.
Marinenko et al., "Precise Coulometric Titrations of Halides," Journal of Research of the National Bureau of Standards—A. Physics and Chemistry, 67a(No. 1):31-35 (1963).
Ozcimder et al., "Organic Elemental Analysis of Small Amounts of Sample by Coulometry, V. Analysis of Organic Chloropesticides," Microchemical Journal. 20(2):227-235 (1975).
Van Oort et al., "Improvement of the Determination of Small Amounts of Chloride by Coulometric Titration," Laboratory for Analytical Chemistry, The University, Croesestr. 77a, Utrecht, The Netherlands. Jun. 1976.
International Search Report mailed Jan. 30, 2024 in International Application No. PCT/US2023/035066.

\* cited by examiner

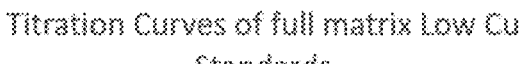
A
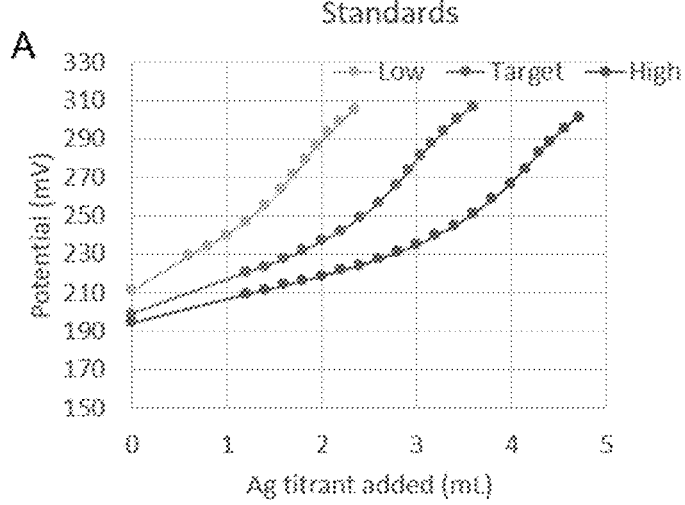
Titration Curves of full matrix Low Cu Standards
B
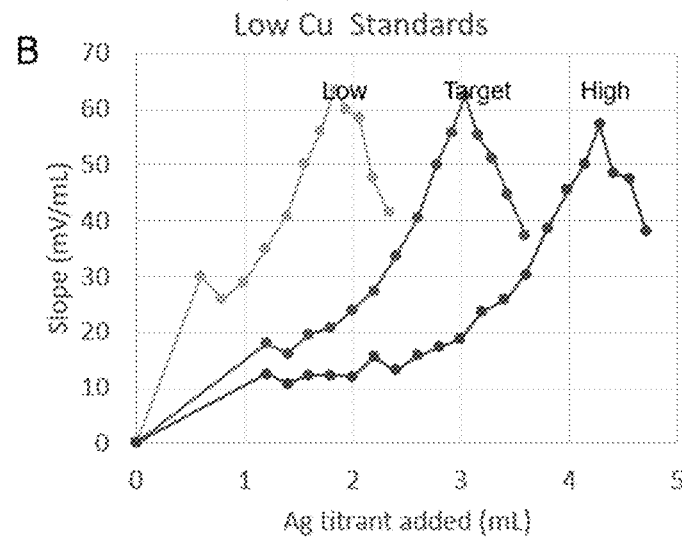
Titration Slope Curves of full matrix Low Cu Standards
C
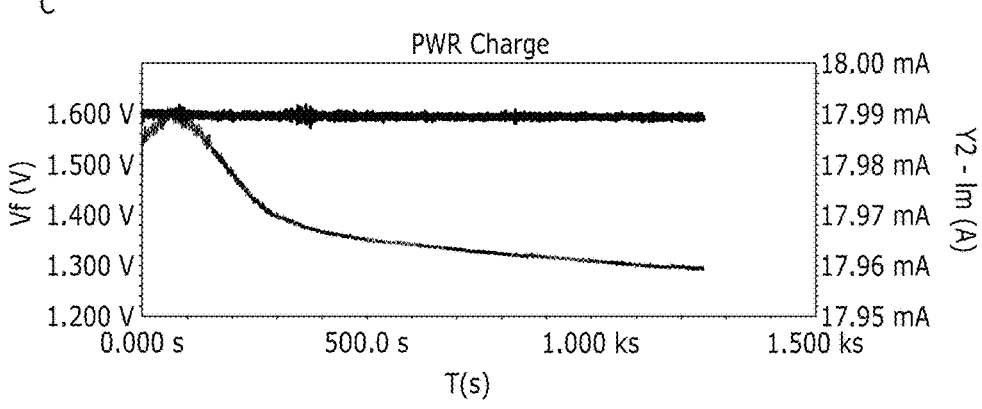
Fig. 2A-2C

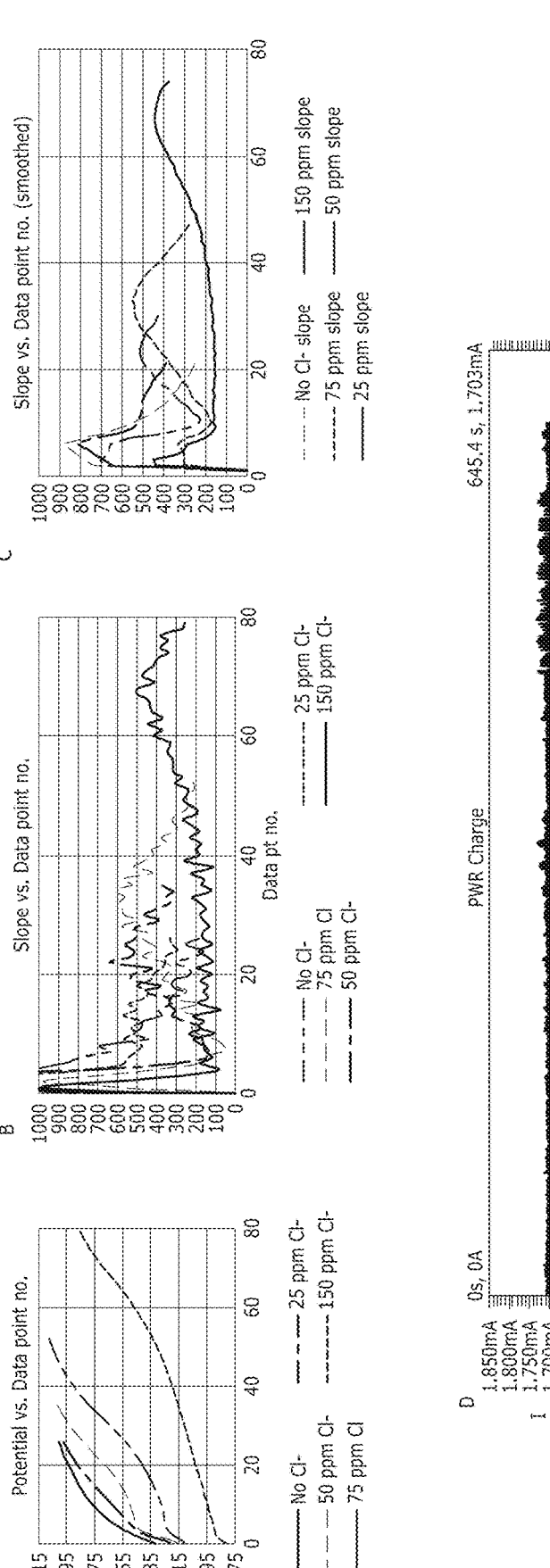
Fig. 3A–3D

NON-REAGENT CHLORIDE ANALYSIS IN ACID COPPER PLATING BATHS

CROSS-REFERENCE TO RELATED APPLICATIONS

This application claims the benefit of U.S. Provisional Application No. 63,417,318, filed on Oct. 18, 2022, which is incorporated herein by reference.

BACKGROUND

The disclosed subject matter relates to analytical chemistry, and more specifically, to a method and system for non-reagent chloride analysis in acid copper plating baths.

Acid copper electroplating baths can contain inorganic major components (for example, copper sulfate, and sulfuric acid) and organic additives whose concentrations must be controlled in the low parts per million range in order to attain certain desired deposit properties and morphology.

In particular, in acid copper electroplating baths, the concentration of chloride ion (typically in the 20 to 100 mg/L range) can be controlled since chloride ions can be essential to the functioning of the additive system. A common and widely used method is potentiometric titration, where the chloride ion is titrated with silver nitrate solution through the reaction Ag (+)+Cl (−)→AgCl (s). The endpoint can be detected using a silver-ion selective electrode which can be readily automated. When using this method in an automatic chemical monitoring system, the silver titrant (e.g., silver nitrate solution) can be purchased and stored in the system. In turn, this requires periodic replacement or replenishment which leads to manual maintenance with potential process tool down time and is not desired for high volume manufacturing processes. Additionally, use of a liquid de-passivator can defeat the objective of not using specialized liquid reagents.

Accordingly, there is a need for a non-reagent chloride analysis method that does not require the use of specialized liquid reagents and improves satisfaction of the semiconductor manufacturing users.

SUMMARY

To solve the problem of nuisance and safety raised by liquid reagents in semiconductor manufacturing environments, the disclosed subject matter provides methods for chloride analysis in acid copper plating baths without need for specialized liquid reagents such as commonly used $AgNO_3$ titrant. Embodiments of the disclosed subject matter provide for generating $Ag^+$ in situ by anodic dissolution of a metallic Ag electrode, for example but not limited to, adding anodic dissolution of Ag electrode into a blend of VMS (Virgin Make-Up Solution) and DIW (Deionized Water).

The disclosed matter provides methods for non-reagent chloride analysis in an acid copper plating bath. An example method includes adding a blend solution including VMS into an acid copper plating bath including Cl⁻, thereby generating an $Ag^+$-containing solution; adding the generated $Ag^+$-containing solution as a silver titrant into an electrolyte including an analysis sample; and analyzing chloride concentration in the sample, via measuring at least one working electrode (WE) potential in a predetermined potential range.

In certain embodiments, the VMS includes at least $CuSO_4$, $H_2SO_4$, or HCl.

In certain embodiments, the blend solution further includes DIW.

In certain embodiments, the concentration of VMS in the blend solution is less than 15% by vol.

In certain embodiments, the WE is Ag ISE (ion selective electrode).

Furthermore, the disclosed subject matters provide an electrochemical system for non-reagent chloride analysis in an acid Cu plating bath.

In certain embodiments, the system includes an $Ag^+$-containing solution generation unit, comprising a potentiostat; an $Ag^+$-containing solution generation cell including an acid copper plating bath; an Ag anode and a cathode, connecting the potentiostat; and a VMS vessel and a DIW vessel, configured to deliver a blend solution of VMS and DIW into the $Ag^+$-containing solution generation cell.

The system can further include a titration unit, including: a titrator, a titration cell containing an Ag ISE and a stirrer, connecting the titrator and the titration cell, a sample vessel and a DIW vessel, configured to deliver a sample solution into the titration cell, and a pump delivering the $Ag^+$-containing solution to the titration cell.

In certain embodiments, the Ag anode is a silver metal wire or rod.

In certain embodiments, the cathode is a platinum wire or stainless-steel rod.

In certain embodiments, the system further includes a computing device having a memory element with a stored algorithm for: delivering VMS at a predetermined concentration into the $Ag^+$-containing the solution generation cell to produce an $Ag^+$-containing solution, delivering $Ag^+$-containing solution at a constant predetermined flow rate from $Ag^+$-containing solution generation cell into the titration cell, scanning the potential of the Ag ISE relative to a reference electrode (RE) at a predetermined positive potential limit at a predetermined potential scan rate, and measuring chloride concentration in the sample.

In certain embodiments, the titration cell connects to a drain downstream.

BRIEF DESCRIPTION OF THE DRAWINGS

FIG. 2A shows an overlay of three different titrations of low Cu standards with differing chloride concentrations, plotting potential versus total volume of titrant added.

FIG. 2B shows the derivatives of the curves in FIG. 2A, plotting the change in potential (i.e., slope) versus volume of titrant added.

FIG. 2C shows a plot of the potential (left vertical axis) and current (right vertical axis) of anodic dissolution of Ag over time.

FIG. 3A shows an overlay of three different titrations with differing chloride concentrations (from 0 to 150 ppm Cl⁻), plotting potential versus total volume of titrant added in the compared example.

FIG. 3B shows the derivatives of the curves in FIG. 3A, plotting the change in potential (i.e., slope) versus volume of titrant added.

FIG. 3C shows the derivatives of the curves in FIG. 3A, smoothly plotting the change in potential (i.e., smoothed slope) versus volume of titrant added.

FIG. 3D shows a plot of Ag discharge with anode passivation eventually occurring in the compared example.

Figure 1:
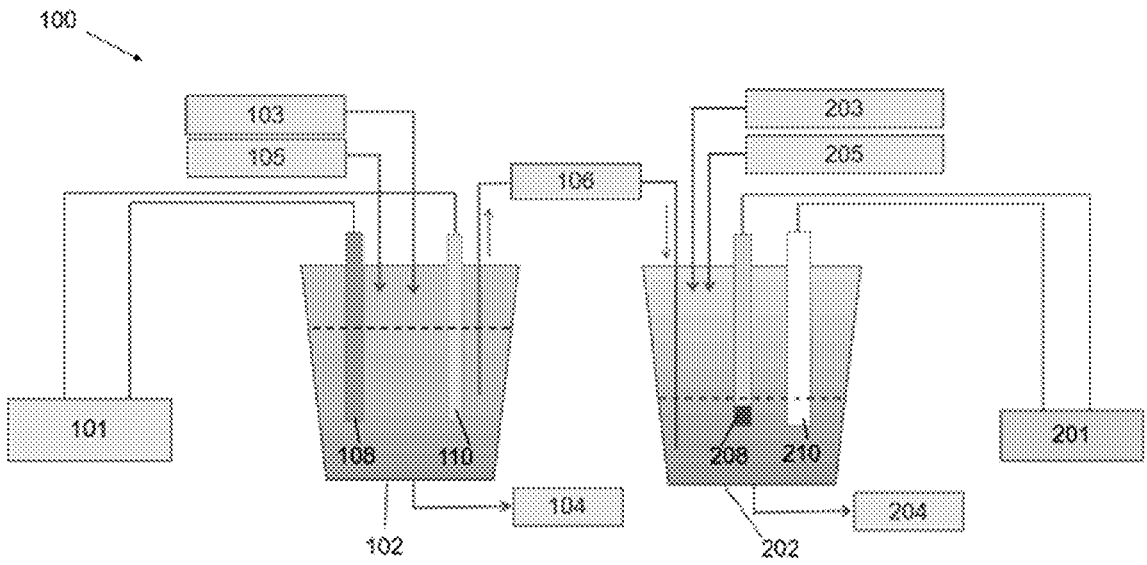
FIG. 1 provides an image showing an exemplary setup of hardware used in an embodiment of the disclosed subject matter.

It is to be understood that both the foregoing general description and the following detailed description are exemplary and are intended to provide further explanation of the disclosed subject matter.

DETAILED DESCRIPTION

The disclosed subject matter provides techniques of using VMS blend solution to generate an $Ag^+$ titrant in an acid copper solution, which can be applied over a variety of industry fields, like analyzing, monitoring, measuring, or determining concentration in $Cl^-$ containing solutions.

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosed subject matter and how to make and use them.

For purposes of interpreting this specification, the following definitions will apply and whenever appropriate, terms used in the singular will also include the plural and vice versa.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and up to 1% of a given value. Alternatively, e.g., with respect to biological systems or processes, the term can mean within an order of magnitude, within 5-fold, and within 2-fold, of a value.

As used herein, the term "electrode potential," or simply "potential," refers to the voltage occurring across a single electrode-electrolyte interface. In practice, the electrode potential often includes an appreciable resistive voltage drop in the electrolyte, which typically remains constant and does not affect voltametric analysis results obtained under the same conditions.

As used herein, the terms "electroplating," "plating," and "electrodeposition" refer to copper electrodeposition and are equivalent. A "plating bath" is employed for practical copper plating and contains organic additives whose concentrations are controlled within ranges, whereas the corresponding "supporting electrolyte" typically has substantially the same inorganic composition, not including chloride ion, as the plating bath but no organic additives. A "background electrolyte" comprises a supporting electrolyte containing one or more organic additives at predetermined concentrations. The concentration of chloride ion in a supporting electrolyte or a background electrolyte may be varied.

As used herein, the term "acid copper electroplating bath" or "acid copper plating bath" refers to a solution used in electroplating processes to deposit a layer of copper onto a substrate through an electrochemical process. This type of electroplating is commonly used to enhance the substrate's properties, provide a decorative finish, or improve its conductivity. The composition of an acid copper electroplating bath can vary depending on the specific application, but here are the typical components found in such a bath: copper salt, sulfuric acid, and additives. In practice, mostly this bath solution includes chloride or $Cl^-$.

As used herein, the term "VMS" refers to Virgin Make-Up Solution. In analytical chemistry and laboratory practices, a "make-up solution" refers to a solution that is prepared to dilute or adjust the concentration of a sample or a reagent. "Virgin Make-Up Solution" likely refers to a freshly prepared or unused solution used to create specific concentrations for calibration, standardization, or sample preparation in experiments. These solutions are often prepared using high-purity chemicals and solvents to minimize any potential contamination.

As used herein, the term "ion-selective electrode (ISE)" refers to a type of electrode that responds selectively to a specific ion in a solution. It measures the activity or concentration of that particular ion in the solution. ISEs are commonly used in analytical chemistry and various fields where accurate ion concentration measurements are essential, such as environmental monitoring, medical diagnostics, and industrial processes. One example of an ion-selective electrode is the Ag ISE in the present disclosure. In the Ag ISE, the electrode responds selectively to chloride ions ($Cl^-$) in the solution. The potential of the electrode is determined by the concentration of chloride ions in the solution.

As used herein, the term "coulometric titration" refers to a specialized type of titration in analytical chemistry that relies on the quantitative measurement of electric charge to determine the amount of substance in a sample. This technique is particularly useful when dealing with substances that cannot be easily detected using traditional visual indicators, as it involves the direct measurement of electrical current. In traditional titrations, a solution of known concentration (titrant) is added incrementally to a solution of analyte until a chemical reaction is complete. The endpoint of the reaction is often detected using indicators that change color. In contrast, in coulometric titration, the endpoint is determined based on the amount of electrical charge required to complete a chemical reaction.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. Ranges disclosed herein, for example, "between about X and about Y" are, unless specified otherwise, inclusive of range limits about X and about Y as well as X and Y. With respect to sub-ranges, "nested sub-ranges" that extend from either endpoint of the range are specifically contemplated. For example, a nested sub-range of an exemplary range of 1 to 50 can include 1 to 10, 1 to 20, 1 to 30, and 1 to 40 in one direction, or 50 to 40, 50 to 30, 50 to 20, and 50 to 10 in the other direction.

As used herein, the term "predetermined concentration" as used herein refers to a known, target, standard or optimum concentration of a component in a solution.

As used herein, the term "selective" or "selectively" refers to, for example, the particular monitoring, measurement, or determination of a characteristic of a specific or particular component. For example, the selective measurement of an ion refers to the measurement of one particular or predetermined target ion from a plurality of the ions present in solution.

As used herein, the term "accurate" or "accurately" refers to, for example, a measurement or determination that is relatively close to or near an existing or true value, standard, or known measurement or value. In certain embodiments, the measurement or determination accuracy error is less than ±0.30%, having a standard deviation less than 0.02, and/or a residual standard deviation (RSD) less than 2%.

As used herein, the term "processing solution" refers to a chemical solution which is used to analyze the concentration of a substance in the solution by reacting it with a known amount of a standard solution. Processing solutions are used in several industries, including electro/electroless plating, metallurgical, chemical, pharmaceutical, and other industries in which measuring, monitoring and control of an analyte is needed.

As used herein, the term "titrant" refers to a standard solution comprising a known concentration of a reagent that chemically reacts with a "reactant" or "unknown species" whose concentration in a sample solution is to be determined. A "titration" is an analytical procedure involving repeated standard addition of a known volume of a titrant solution to an analysis solution (comprising the sample solution), coupled with monitoring the concentration of an indicator species, which participates in the reaction between the titrant and the reactant, or is indirectly affected by this reaction.

As used herein, the term "equivalence point" refers to the point in a titration at which the reaction between the titrant and the reactant is complete, corresponding to a stoichiometric balance between the number of moles of the titrant and the number of moles of the reactant with respect to formation of a compound or complex.

As used herein, the term "titration endpoint" refers to a relatively rapid change in the concentration of the indicator species as additional titrant is added to the analysis solution after the equivalence point has been reached. The concentration of the unknown species in the sample solution can be calculated from the volume of titrant solution added to the analysis solution at the equivalence point (approximately equivalent to the endpoint).

As used herein, the term "titration curve" refers to a plot of the concentration of a titration indicator species in an analysis solution, or a parameter proportional to this concentration, as a function of the volume of titrant solution added to the analysis solution. It can be more convenient to utilize a concentration parameter that is proportional to the concentration of the indicator species, especially when the indicator species participates in a complexation reaction involving competing complexing agents. The endpoint for the titration can be determined from a curve feature corresponding to a rapid change in the concentration of the indicator species, such as a curve knee or inflection point. Detection of the titration endpoint can be facilitated by differentiating the titration curve, which converts an inflection point into a peak. Titration data can be handled as titration curves or plots, but such data can be tabulated and used directly, e.g., by a computer, and the term "titration curve" includes tabulated data.

As used herein, the term "potentiostat" refers to an electronic device for controlling the potential of a WE by passing current between the WE and a counter electrode so as to drive the WE to a desired potential relative to a reference electrode. Use of a potentiostat avoids passing appreciable current through the reference electrode, which can change its potential. Operation in the multiple mode may also reduce errors in the electrode potential associated with the resistive voltage drop in the electrolyte.

The present disclosure provides a method and a system for determining the concentration of chloride ion in an acid copper plating bath sample. The embodiments of the present disclosure are suitable for analysis of acid copper plating baths comprising anions selected from the group consisting of $Cu^+$, $Cl^-$, sulfate, fluoroborate, sulfamate, alkyl sulfonate, and mixtures thereof.

In the acid copper plating baths of exemplary embodiments, chloride ion (CO is typically present at very low concentration in the range from 20 to 100 mg/L (ppm) so that electrochemical oxidation of chloride ion generally occurs under some degree of diffusion control. The conventional $Cl^-$ analysis method implements a potentiometric titration, typically using $Ag^+$ (e.g., $AgNO_3$) as titrant and Ag ISE (ion selective electrode) for end point detection, under the following chemical reaction equation: $Ag^+ + Cl^- \rightarrow AgCl$ (s), wherein at equivalent point, $Cl^-$ in sample equals to $Ag^+$ titrant added. Such a direct coulometric titration of chloride in a sample where silver ion is generated insitu from silver anode did not work properly due to anode passivation. For example, the anode is covered with a film of silver chloride solid, and cannot perform the analysis sustainably.

The objective of the present disclosure is to develop methods and systems for chloride analysis without the need for an external and specialized liquid reagent, such as commonly used $AgNO_3$ titrant to avoid liquid nuisance and safety concerns in semiconductor manufacturing environment.

In an embodiment, an exemplary non-reagent method for chloride analysis in acid copper plating baths is provided. The method includes adding a blend solution including VMS into an acid Cu plating bath including $Cl^-$, thereby generating a solution, adding the generated solution as a silver titrant into an electrolyte including an analysis sample, measuring chloride quantitation for at least one WE potential in a predetermined potential range, where the chloride quantitation can include a measurement of the chloride concentration in the sample.

Optionally, in some embodiments, VMS may include at least $CuSO_4$, $H_2SO_4$, or HCl. The blend solution may further comprise DIW. The concentration of VMS in the blend solution is at a predetermined concentration, for example, but not limiting to, less than 15% by vol. The concentration of $Cl^-$ in the plating bath is at a predetermined concentration, for example, but not limiting to, 20-100 ppm. The WE may be an Ag ISE.

The present disclosure further provides an electrochemical system for automated application of the above measurement method for non-reagent chloride in acid Cu plating bath. The apparatus comprises a computing device that is interfaced with suitable electronic and mechanical equipment, and includes a memory element with a stored algorithm operative to affect the method. The stored algorithm may also be operative to apply the calibration of the above measurement method. The computing device may comprise a computer with integrated components, or may comprise separate components, such as a microprocessor and a memory device that includes the memory element, for example. The memory element may be of any suitable type, including computer hard drive, microprocessor chip, read-only memory (ROM) chip, programmable read-only memory (PROM) chip, magnetic storage device, computer disk (CD) and digital video disk (DVD), for example.

The stored algorithm of the electrochemical system of the present disclosure may also be operative to apply a measurement, comprising but not limiting to, generating a standard curve by repeating the flowing the plating bath sample, scanning the potential of the WE and measuring current for a plurality of chloride standard solutions comprising a background electrolyte of the plating bath sample with different known concentrations of chloride ion, and comparing the chloride current parameter provided in the measuring with the standard curve to determine the concentration of chloride ion in the plating bath sample.

Suitable electrochemical analysis systems, computing devices, memory elements, and interfaces for use in the embodiment are well known to those skilled in the art. In some embodiments, the electrochemical analysis system of the apparatus of the invention further includes a pump and suitable plumbing for flowing the plating bath sample over the surface of a stationary WE at a constant flow rate, and/or delivering the sample to different cells as needed.

FIG. 1 shows a schematic representation of an exemplary electrochemical system 100 of the embodiment, which has two units, an $Ag^+$-containing generation unit and a titration unit. In the $Ag^+$-containing solution generation unit, an electronic potentiostat 101 is used to control the potential of a WE (cathode 110) by passing current between it and a counter electrode (CE) (Ag anode 108) so as to drive it to a desired potential. These electrodes are immersed in an acid Cu plating bath solution contained in $Ag^+$-containing solution generation cell 102. The plating bath solution in the $Ag^+$-containing solution generation cell 102 can include $Cu'$, $Cl^-$, and sulfate, etc. However, the embodiment may be practiced using any other suitable device for controlling the potential of the WE. The tip of the RE, or an extension thereof, can be located as close as practical to the WE so as to minimize errors in the WE potential associated with solution resistance. Certain commercial potentiostats include a current follower device (not shown) to avoid errors in the potential of the WE associated with the resistance of the current measuring device.

As depicted in FIG. 1, the electrochemical system 100 further comprises a DIW vessel 103 and a VMS vessel 105, which are configured to deliver the blend of VMS and DIW into the $Ag^+$-containing solution generation cell 102 via a motor mechanism, e.g., a pump. Additionally, a drain 104 can be downstream mounted on the $Ag^+$-containing solution generation cell 102.

To implement a non-reagent chloride analysis in a sample, the electrochemical system further includes a titration unit. In the titration unit, a titrator 201 is used to titrate $Ag^+$ in a sample solution. Similar, a titration cell 202 is setup to have an Ag ISE 208 and a stirrer 210. A sample solution in a sample vessel 205 can be delivered to the electrolyte in the titration cell 202, via pumps. Between the $Ag^+$-containing solution generation cell 102 and titration cell 202, there is a pump 106 to deliver the resulting $Ag^+$-containing solution which can in principle be used to titrate the chloride in the sample solution, as any commercially available silver solution can, like, for example, an external silver nitrate reagent. Since both copper and silver ions can be reduced and deposited to the cathode during the dissolution process, reaction parameters were optimized to maximize the silver ion concentration and the dissolution efficiency, including but not limited to electrolysis current, potential, time. VMS percentage, etc.

The composition of acid copper electroplating baths varies significantly depending on the type of bath and the supplier. For example, high-acid baths typically contain 30-60 g/L copper (as in copper sulfate), 60-240 g/L sulfuric acid and 25-100 ppm chloride ion. Low-acid baths typically contain 0.5-60 g/L copper (as in copper sulfate), 1-15 g/L sulfuric acid and 25-100 ppm chloride ion. Acid copper plating bath additives are generally proprietary formulations supplied in the form of solutions that may contain more than one additive species or combination of additives. The chemical nature and concentrations of the additive species may be changed from time to time by the supplier without notice.

EXAMPLE

The efficacy of the present disclosure for determining the concentration of chloride ion in an acid copper bath sample was demonstrated for the Low Acid ViaForm™ (Enthone, Inc.) acid copper sulfate plating bath. The supporting electrolyte contains low Cu chemistry (e.g., 5 $Cu^{2+}$-10 g/L $H_2SO_4$-50 ppm $Cl^-$). The background electrolyte comprised the supporting electrolyte with a suppressor, accelerator (anti-suppressor), and leveler additives at the concentrations recommended by the bath supplier. Voltametric measurements were made under potentiostatic control using a Qualilab QL-10® plating bath analyzer (ECI Technology, Inc.). During measurements, the solution temperature was controlled at 25° C. within ±0.1° C.

In the example, a blend of VMS with DPW (VMS/DIW ratio: 0.1-0.2, e.g., VMS 6 mL and DM 44 mL) is added into an $Ag^+$-containing solution generation cell to generate $Ag^+$-containing solution. During the generation process, over the Ag anode surface in the titration cell, silver metal is oxidized and thus dissolved to the electrolyte, $(Ag(s)+e-→Ag^+)$. Corresponding to the above chemical reaction equation, the acid copper sulfate plating bath (25° C.) in the Agt containing solution generation cell results in $Ag^+$-containing solution, which is used to titrate the chloride in a sample solution (3-10 mL). The sample solution ill the titration cell (25° C.) in different embodiments contains the expected three low (30 ppm), target (50 ppm) and high (70 ppm) chloride concentrations. For the following titration, the generated $Ag^+$-containing solution as a titrant in the titration cell continuously provides sustainable Ag anode usage with low tool maintenance and eliminates the need for an external reagent. Additionally, circumventing the need for a reagent eliminates the related manual maintenance and replenishment. The endpoint in the example is detected via scanning the potential of the Ag ISE. At that point, the amount of $Cl^-$ in the sample equals to the amount of $Ag^+$ delivered by the titrant added.

FIG. 2A shows an overlay of three different titrations of low Cu standards with differing chloride concentrations, plotting potential versus total volume of titrant added. FIG. 2B shows the derivatives of the curves in FIG. 2A, plotting the change in potential (i.e., slope) versus volume of titrant added. FIG. 2C shows a plot of the potential (left vertical axis) and current (right vertical axis) of anodic dissolution of Ag over time.

Table 1 shows the titration metrics of the three expected concentrations.

TABLE 1

|  | Low | Target | High |
| --- | --- | --- | --- |
| Average Vend (mL) | 1.7685 | 2.9645 | 4.1365 |
| Expected Cl (ppm) | 30 | 50 | 70 |
| Calculated Cl (ppm) | 29.93 | 50.14 | 69.93 |
| Error | −0.22% | 0.27% | −0.10% |
| RSD | 1.63% | 0.17% | 1.93% |

Illustrated in FIGS. 2A-2C and Table 1, the non-reagent titration measurement of chloride of the present disclosure demonstrates a strong endpoint inflection, an efficient silver dissolution in the sample without a negative impact, and more accurate measurement data with less error and RSD.

In contrast, a compared example, known in the art, is conducted using a direct coulometric titration of chloride in the sample solution where silver ion is generated insitu from the silver anode and does not work properly due to anode passivation, without the usage of VMS. Instead, a potentiometric titration uses $Ag^+$ (e.g., $AgNO_3$) as an external titrant and an Ag ISE for end point detection.

FIG. 3A-3D illustrate the resultant curves of the compared example without the usage of VMS. FIG. 3A shows an overlay of three different titrations with differing chloride concentrations (from 0 to 150 ppm $Cl^-$), plotting potential versus total volume of titrant added in the compared example. FIG. 3B shows the derivatives of the curves in FIG. 3A, plotting the change in potential (i.e., slope) versus volume of titrant added. FIG. 3C shows the derivatives of the curves in FIG. 3A, smoothly plotting the change in potential (i.e., smoothed slope) versus volume of titrant added. FIG. 3D shows a plot of Ag discharge with anode passivation eventually occurring in the compared example.

Unlike the non-reagent titration using VMS in the present disclosure, such a direct titration using external titrant results in a noisy titration curve with weak end point inflection (as shown in FIG. 3A), an inaccurate end point detection without post data processing (as shown in FIG. 3B and FIG. 3C), an insufficient inflection for samples with low level of chloride (e.g., 25 ppm), a noisy data plot of Ag discharge with anode passivation eventually leading to failure (as shown in FIG. 3D). Various modifications and alterations to the described embodiments will be apparent to those skilled in the art in view of the teachings herein. Accordingly, the disclosure herein is intended to be illustrative, but not limiting, of the scope of the disclosed subject matter. Moreover, the principles of the disclosed subject matter can be implemented in various configurations and are not intended to be limited in any way to the specific embodiments presented herein.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

What we claim is:

1. A method for non reagent chloride analysis in an acid copper plating bath, comprising:
adding a blend solution including VMS (Virgin Makeup Solution) into an acid copper plating bath including Cl, and generating an anodic dissolution of an Ag electrode into the plating bath, thereby generating an $Ag^+$-containing solution in an $Ag^+$-containing solution generation cell separate from a titration cell;

transferring, via a pump, adding the generated $Ag^+$-containing solution as a silver titrant from the $Ag^+$-containing solution generation cell into an electrolyte including an analysis sample in the titration cell; and
analyzing chloride concentration in the sample, via measuring at least one working electrode (WE) potential in a predetermined potential range.

2. The method of claim 1, wherein the VMS includes at least $CuSO_4$, $H_2SO_4$, and/or HCl.

3. The method of claim 1, wherein the blend solution further comprises DIW (Deionized Water).

4. The method of claim 1, wherein concentration of VMS in the blend solution is less than 15% by volume.

5. The method of claim 1, wherein the WE is an Ag (ISE).

6. An electrochemical system for non reagent chloride analysis in acid Cu plating bath, comprising:
an $Ag^+$-containing solution generation unit, comprising:
a potentiostat;
an $Ag^+$-containing solution generation cell including an acid copper plating bath;
an Ag anode and a cathode connected to the potentiostat; and
a VMS vessel and a DIW vessel, configured to deliver a blend solution of VMS and DIW into the $Ag^+$-containing solution generation cell,
a titration unit, comprising:
a titrator,
a titration cell containing an Ag ISE (ion selective electrode) and a stirrer, connecting the titrator and the titration cell, and
a sample vessel and a DIW vessel, configured to deliver a sample solution into the titration cell,
and
a pump delivering the Ag-containing solution from the $Ag^+$-containing solution generation cell to the titration cell.

7. The system of claim 6, wherein the Ag anode is a silver metal wire or rod.

8. The system of claim 6, wherein the cathode is a platinum wire or stainless-steel rod.

9. The system of claim 6, wherein the system further comprises a computing device having a memory element with a stored algorithm operative for
delivering VMS at a predetermined concentration into the $Ag^+$-containing solution generation cell to produce the $Ag^+$-containing solution,
delivering the $Ag^+$-containing solution at a constant predetermined flow rate from the $Ag^+$-containing generation cell into the titration cell,
scanning potential of the Ag ISE electrode relative to a reference electrode at a predetermined positive potential limit at a predetermined potential scan rate, and
measuring chloride concentration in the sample.

10. The system of claim 6, wherein the titration cell is connected to a drain downstream thereof.

* * * * *